US009320659B2

(12) United States Patent
Richardson

(10) Patent No.: US 9,320,659 B2
(45) Date of Patent: Apr. 26, 2016

(54) METHOD OF USING A DIAPER WITH A FOLD THEREIN

(71) Applicant: Darryl Richardson, Hoover, AL (US)

(72) Inventor: Darryl Richardson, Hoover, AL (US)

( * ) Notice: Subject to any disclaimer, the term of this patent is extended or adjusted under 35 U.S.C. 154(b) by 88 days.

(21) Appl. No.: 14/161,404

(22) Filed: Jan. 22, 2014

(65) Prior Publication Data

US 2014/0135728 A1    May 15, 2014

Related U.S. Application Data

(62) Division of application No. 12/760,198, filed on Apr. 14, 2010, now abandoned.

(51) Int. Cl.
| A61F 13/49 | (2006.01) |
| A61F 13/493 | (2006.01) |
| A61F 13/511 | (2006.01) |
| A61F 13/84 | (2006.01) |
| A61F 13/15 | (2006.01) |

(52) U.S. Cl.
CPC ......... *A61F 13/493* (2013.01); *A61F 13/15203* (2013.01); *A61F 13/511* (2013.01); *A61F 13/84* (2013.01)

(58) Field of Classification Search
CPC . A61F 13/15747; A61F 13/474; A61F 13/49; A61F 13/49001; A61F 13/493; A61F 13/55115
USPC ............. 604/385.01, 385.06, 385.14–385.16, 604/385.19, 385.201; 2/402
See application file for complete search history.

(56) References Cited

U.S. PATENT DOCUMENTS

| 4,230,113 A * | 10/1980 | Mehta ...................... 604/385.09 |
| 4,698,855 A * | 10/1987 | Hicks ................................ 2/402 |
| 4,883,481 A * | 11/1989 | Blanchard ................ 604/385.11 |
| 6,652,499 B1 * | 11/2003 | Edgren et al. ............ 604/385.01 |
| 6,824,537 B1 * | 11/2004 | Samuelsson ........... 604/385.201 |
| 7,931,635 B1 * | 4/2011 | Gaston ................... 604/385.201 |
| 2005/0055007 A1 * | 3/2005 | Kawata et al. ........ A61F 13/493 604/387 |

FOREIGN PATENT DOCUMENTS

EP            0405403 A2 *  1/1991

* cited by examiner

*Primary Examiner* — Lynne Anderson
*Assistant Examiner* — Kathryn E Ditmer
(74) *Attorney, Agent, or Firm* — C. Brandon Browning; Maynard Cooper & Gale

(57) ABSTRACT

An expandable diaper having storage for containing wipes, the diaper including a front end and a back end, opposing lateral edges extending between the front end and the back end, each of the opposing lateral edges including an inwardly curved portion configured for engaging a wearer's leg, a liquid impermeable outer layer, a liquid permeable, exposed inner layer, an absorbent material disposed between the outer layer and the inner layer, and a longitudinal fold formed in the inner layer extending between the front end and the back end and between the opposing lateral edges. An adhesive is applied within the fold, and is configured for allowing the fold to be pulled apart when desired for increasing a width of the diaper. A pocket is located about the front end of the diaper for storing a plurality of moist wipes.

13 Claims, 2 Drawing Sheets

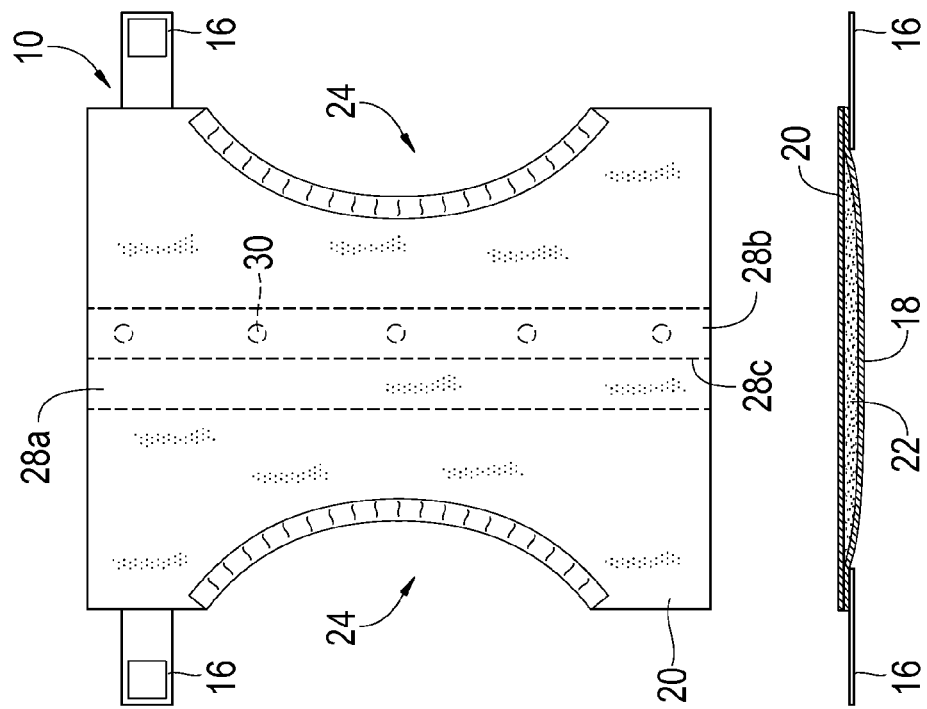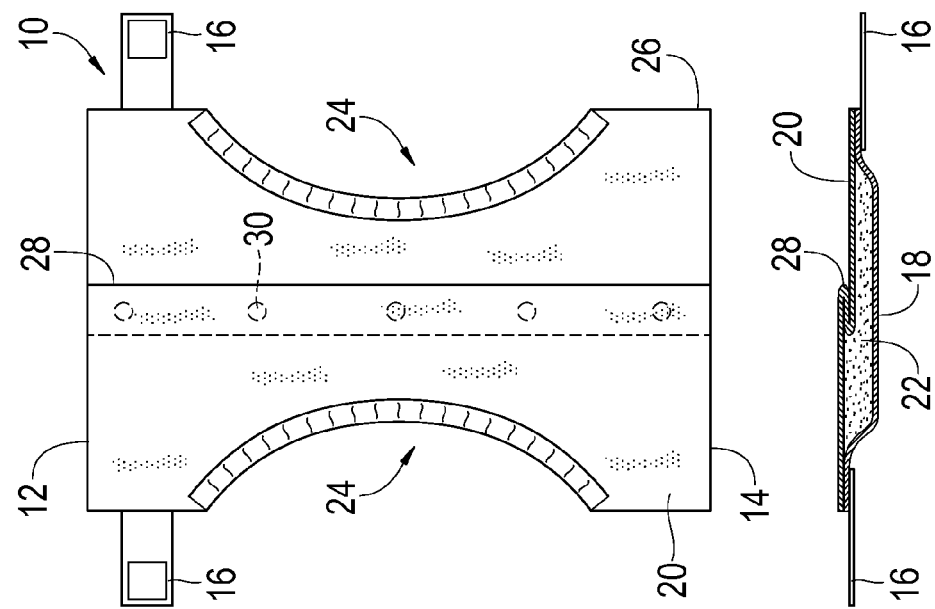

METHOD OF USING A DIAPER WITH A FOLD THEREIN

This application is a divisional of and claims priority to U.S. Nonprovisional patent application Ser. No. 12/760,198, filed on Apr. 14, 2010, and titled "Diaper and Method of Using Same," which claims priority to U.S. Provisional Patent Application Ser. No. 61/272,956, filed on Nov. 23, 2009, and titled "Extended Baby Care Diaper," the entire contents of both applications being incorporated herein by reference.

FIELD OF INVENTION

The present invention relates to a diaper and method of using same, and more particularly, to a diaper and method of using same for absorption and containment of bodily discharges, the diaper being configured for expanding laterally for accommodating larger wearers and storing items such as wipes for cleansing the wearer.

BACKGROUND OF THE INVENTION

It is well known that diapers must be frequently changed, and a wearer's skin cleansed between changes. For this reason, cleansing cloths or wipes are needed for each diaper change, but a parent or caregiver may be out of, or unable to locate, wipes when a diaper change is needed. In addition, wipes are generally pre-moistened for convenience, and require a leak proof container to keep the wipes from drying out and to protect surrounding surfaces from the moist wipes. Often, these containers are left opened allowing an entire container full of wipes to dry out thereby becoming less effective. In addition, other diaper administering items may be needed, such as powder or lotions, and which also require a separate container for storage. It is also well known that diaper wearers, most often infants, can grow at such rates that they outgrow the diapers purchased for them thereby leaving a parent or caregiver with an unusable supply of outgrown diapers.

SUMMARY OF THE INVENTION

The claimed invention is directed to a diaper system and method of using same that includes a pocket for containing wipes and an extendable lining allowing for increasing the size of the diaper, thus eliminating the need for additional, larger size diapers. In one aspect of the invention there is provided a longitudinal gusset fold in the lining of the diaper defining a pair of gusset panels that overlie one another and are held flat in place by a weak bonding adhesive. This longitudinal gusset fold may be unfolded by pulling apart the fold and thus extending the lining of the diaper laterally and widening the diaper to accommodate a larger size wearer. In another aspect of the invention there is provided a diaper and method for using same which integrally contains its own wipe supply, or supply of other diaper administering items, in a sealed leak proof pouch, thus eliminating the need for separate wipes and other diaper administering items and separate containers for same.

Other objects will become apparent in the following detailed description.

BRIEF DESCRIPTION OF THE DRAWINGS

FIG. 4 is a top plan view of the diaper of FIG. 1.

FIG. 5 is a sectional view of the diaper of FIG. 4.

FIG. 6 is a top plan view of the diaper of FIG. 2.

FIG. 7 sectional view of the diaper of FIG. 6.

DETAILED DESCRIPTION OF THE DRAWINGS

Figure 1:
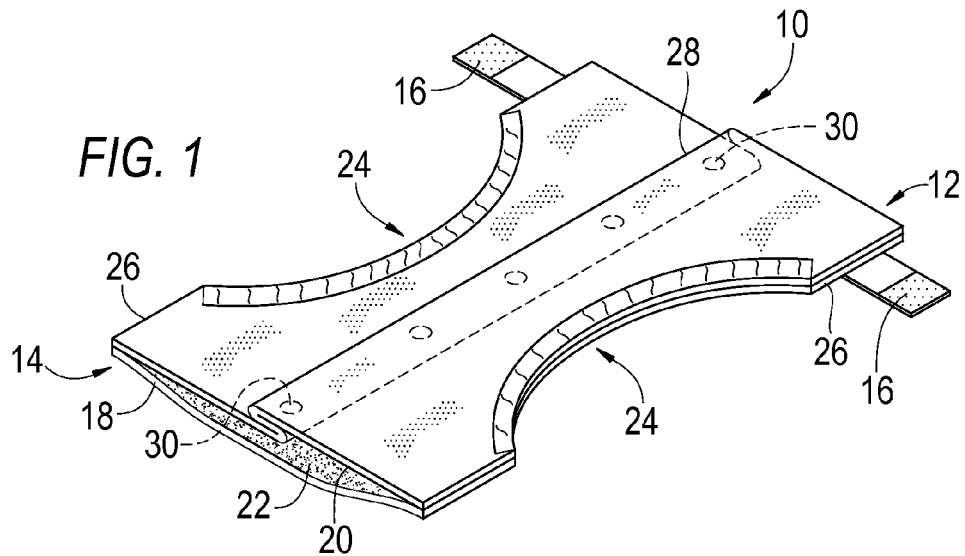
FIG. 1 is a perspective view of diaper according to a preferred embodiment of the present invention.

FIGS. 1 through 7 depict a diaper 10 in accordance with a preferred embodiment of the present invention invention. As depicted in the figures, diaper 10 is of conventional construction having a back end 12 for covering a wearer's backside, a front end 14 for covering the wearer's front side and a pair of closure tabs 16 for coupling front end 14 and back end 16 about wearer. Diaper 10 is constructed of conventional diaper materials including a liquid impermeable outer layer 18, a liquid impermeable, exposed inner layer 20 and an absorbent material 22 disposed between inner layer 20 and outer layer 18. A pair of inwardly curved portions 24 are formed along opposing lateral edges 26 of diaper 10 for receiving and engaging the wearer's leg. Diaper 10 departs from conventional diapers however in its ability to expand laterally for accommodating different sized wearers. This is accomplished by providing a gusset fold in diaper 10 that can be pulled apart to increase the width of the diaper.

More particularly, referring to FIGS. 1, 4 and 5, there is depicted diaper 10 having formed within inner layer 20 a longitudinal gusset fold 28 extending to and between front end 14 and rear end 12. Fold 28 is composed of right and left gusset panels, 28a and 28b, respectively, that are joined along a fold line 28c. Preferably, fold line 28c extends the entire length of diaper 10 and gusset panels 28a and 28b are of sufficient width to allow inner layer 20 to increase in width up to 0.5 inch when fold 28 is expanded or pulled apart. During manufacture of diaper 10, a weak bonding adhesive 30 is placed on one or both of gusset panels 28a and 28b which are then folded along gusset fold line 28c and pressed together to adhesively secure gusset panels 28a and 28b in an overlying, folded flat position. With gusset fold 28 in folded flat position, diaper 10 is narrowed to fit smaller wearers. In this narrowed arrangement, diaper 10 is at least one full diaper size smaller than when fold 28 is pulled apart and inner lining 20 expanded.

Adhesive 30 may be composed of any commercially available material so long that it does not adversely affect the wearer and holds fold 28 intact during regular use by a wearer while being sufficiently weak to allow fold 28 to be unfolded when desired. Depending on the adhesive strength of adhesive 30, it may be dispensed in the form of dots as illustrated in FIGS. 1, 2, 4 and 6, or it may take the form of strips, patches or other configurations so long as it is weakly bonds gusset panel 28a and 28b together in a manner allowing fold 28 to be selectively maintained or pulled apart and unfolded as desired.

Figure 2:
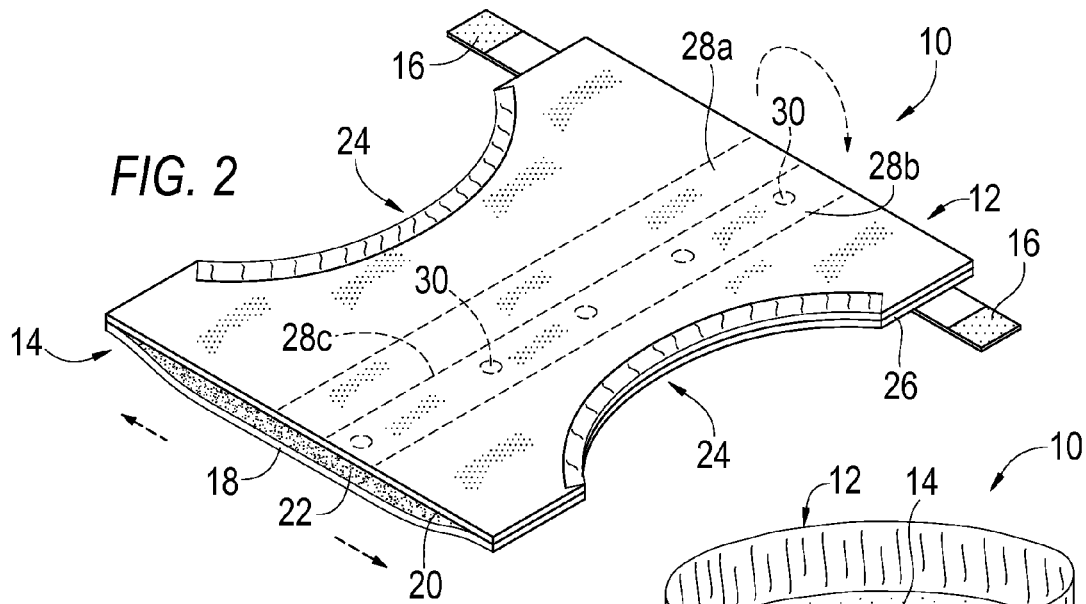
FIG. 2 is a perspective view of the diaper of FIG. 1 illustrating the diaper in an expanded configuration.

FIGS. 2, 6 and 7 depict diaper 10 in the unfolded configuration. With gusset fold 28 unfolded, diaper 10 is widened laterally to fit larger wearers. To increase the size of diaper 10 to accommodate a larger diaper wearer, gusset panels 28a and 28b of inner lining 20 are manually pulled apart prior to diaper 10 being applied to the wearer thus releasing weak bonding adhesive 30 along gusset fold 28. In this manner, fold 28 is unfolded and inner layer 20 is widened.

Figure 3:
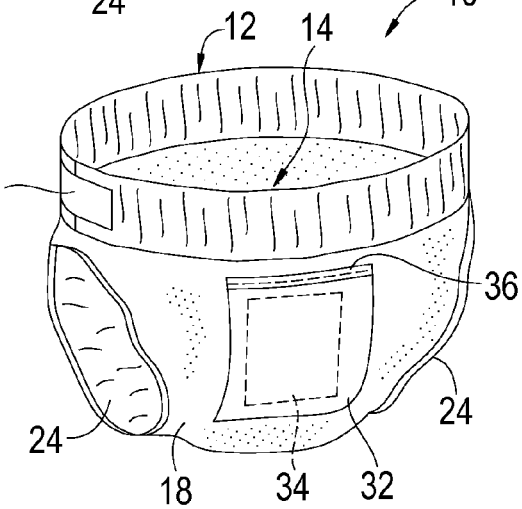
FIG. 3 is a perspective view of a front side of the diaper of FIG. 1 in a fastened position and illustrating a pocket.

To further enhance the usefulness of diaper 10, it is contemplated that diaper 10 may include a pocket 32 for containing a plurality of moist wipes 34. This embodiment of diaper 10, as depicted in FIG. 3, includes pocket 32 arranged about front end 14 of the diaper. Pocket 32 includes a selectively sealable opening 36 through which wipes 34 can be accessed. To ensure that wipes 34 remain moist, pocket 32 is constructed of water impermeable materials, including for example, outer layer 18, which forms the backside of pocket 32. The front side of pocket 32 can be made from an additional layer of impermeable fabric or, the front side can be formed from the fabric layer to which closure tabs 16 are configured to attached. Opening 36 can be sealable using any sealing system known in the art so long as the system prevents the migration of moisture into or out of the pocket. In addition to or in place of wipes 34, pocket 32 can be used to store other diaper administering items, such as powder or lotion.

Pocket 24 may be unsealed at opening 36 to remove wipes 34 from pocket 32 for cleansing of the diaper wearer. In a preferred embodiment, opening 36 may be resealed to preserve any unused wipes or other diaper administering items. Pocket 32 may be exterior to outer layer 18 or may extend between outer layer 18 and inner layer 20, or may be integrally formed with the outer layer.

Modifications and other embodiments of the invention will be apparent to those skilled in the art to which this invention relates having the benefit of the foregoing teachings, descriptions and drawings the present invention is not limited to the specific embodiments disclosed, but is to include modifications and other embodiments which are within the scope of the appended claims.

It is claimed:

1. A method of using a diaper comprising:
    providing a diaper including,
        a front end and a back end, opposing lateral edges extending between the front end and the back end, each of the opposing lateral edges including an inwardly curved portion configured for engaging a wearer's leg,
        a liquid impermeable outer layer,
        a liquid permeable, exposed inner layer,
        an absorbent material disposed between the outer layer and the inner layer,
        a longitudinal fold formed in the inner layer extending to and between the front end and the back end and positioned between the opposing lateral edges, wherein the longitudinal fold does not include the liquid impermeable outer cover layer, and
        an adhesive applied within the longitudinal fold that renders the longitudinal fold to be selectively releasable thereby providing the diaper with a first width when the longitudinal fold is intact and a second width when the longitudinal fold is unfolded, and
    pulling the longitudinal fold apart by hand thereby unfolding the longitudinal fold and providing the diaper with the second width.

2. The method according to claim 1 wherein the longitudinal fold is centrally located between the opposing lateral edges.

3. The method according to claim 1 wherein the first width provides the diaper with a first size and the second width provides the diaper with a second size, the second size being configured for accommodating a larger size wearer than that of the first size.

4. The method according to claim 1 wherein the longitudinal fold does not include the absorbent material.

5. A method of using a diaper comprising:
    providing a diaper including,
        a front end and a back end,
        opposing lateral edges,
        a liquid impermeable layer,
        a liquid permeable layer,
        an absorbent material disposed between the liquid permeable layer and the liquid impermeable layer,
        a fold in the liquid permeable layer extending to and between the front end and the back end and positioned between the opposing lateral edges, the fold forming a substantially S-shaped cross-section that is maintained by a selectively releasable adhesive, wherein the fold does not include the liquid impermeable layer, and
    pulling the fold apart by hand thereby unfolding the fold.

6. The method according to claim 5 wherein increasing the width of the diaper increases a wearer size range that can be accommodated by the diaper.

7. The method according to claim 5 wherein the fold does not include the absorbent material.

8. The method according to claim 5 wherein the fold is centrally located between the opposing lateral edges.

9. A method of using a diaper that is configured for accommodating a first wearer size and a second wearer size that is greater than the first wearer size comprising:
    converting the diaper from a first configuration that is adapted and arranged to accommodate the first wearer size to a second configuration that is adapted and arranged to accommodate the second wearer size by unfolding a selectively releasable fold that extends longitudinally between a front end and a back end of the diaper,
    wherein the diaper includes an outer layer, an inner layer, an absorbent material disposed between the outer layer and the inner layer, and an adhesive applied within the longitudinal fold that renders the longitudinal fold to be selectively releasable,
    wherein the longitudinal fold is formed in the inner layer, wherein the longitudinal fold does not extend through the outer layer, and wherein the longitudinal fold extends along a centerline of the inner layer.

10. The method according to claim 9 further comprising unfolding the selectively releasable fold prior to the diaper being worn by a user.

11. The method according to claim 9 further comprising placing the diaper on a wearer while the diaper is in the second configuration.

12. The method according to claim 9 further comprising unfolding the selectively releasable fold by hand.

13. The method according to claim 9 further comprising increasing a width of the diaper by unfolding the selectively releasable fold, the width being measured between opposing lateral edges of the diaper.

* * * * *